US012668625B2

(12) United States Patent
Sun et al.

(10) Patent No.: US 12,668,625 B2
(45) Date of Patent: Jun. 30, 2026

(54) METHOD FOR TREATING AUTOIMMUNE DISEASE BY IL-17 ANTAGONIST

(71) Applicants: JIANGSU HENGRUI MEDICINE CO., LTD., Lianyungang (CN); SHANGHAI HENGRUI PHARMACEUTICAL CO., LTD., Shanghai (CN)

(72) Inventors: Piaoyang Sun, Lianyungang (CN); Lianshan Zhang, Lianyungang (CN); Jianwen Chen, Lianyungang (CN); Qian Xu, Lianyungang (CN); Qunjie Gao, Lianyungang (CN)

(73) Assignees: JIANGSU HENGRUI MEDICINE CO., LTD., Lianyungang (CN); SHANGHAI HENGRUI PHARMACEUTICAL CO., LTD., Shanghai (CN)

( * ) Notice: Subject to any disclaimer, the term of this patent is extended or adjusted under 35 U.S.C. 154(b) by 1188 days.

(21) Appl. No.: 17/631,289

(22) PCT Filed: Jul. 29, 2020

(86) PCT No.: PCT/CN2020/105510
§ 371 (c)(1),
(2) Date: Jan. 28, 2022

(87) PCT Pub. No.: WO2021/018191
PCT Pub. Date: Feb. 4, 2021

(65) Prior Publication Data
US 2022/0267432 A1 Aug. 25, 2022

(30) Foreign Application Priority Data
Jul. 30, 2019 (CN) .......................... 201910695261.2
Jun. 10, 2020 (CN) ......................... 202010523393.X

(51) Int. Cl.
*A61K 39/395* (2006.01)
*A61P 19/02* (2006.01)
*A61P 37/02* (2006.01)
*C07K 16/24* (2006.01)
*A61K 39/00* (2006.01)

(52) U.S. Cl.
CPC ........ *C07K 16/244* (2013.01); *A61K 39/3955* (2013.01); *A61P 19/02* (2018.01); *A61P 37/02* (2018.01); *A61K 2039/505* (2013.01)

(58) Field of Classification Search
CPC .......................... A61K 39/3955; C07K 16/244
See application file for complete search history.

(56) References Cited

U.S. PATENT DOCUMENTS 9,717,791 B2 8/2017 Guettner et al.
2009/0175881 A1 7/2009 Presta et al.
2011/0038878 A1 2/2011 Presta et al.
2011/0052596 A1 3/2011 Presta et al.
2011/0236390 A1 9/2011 Almagro et al.
2015/0104457 A1 4/2015 Alberici et al.
2015/0175692 A1 6/2015 Di Padova et al.
2016/0039928 A1 2/2016 Di Padova et al.
2016/0289321 A1 10/2016 Zhang et al.
2017/0198035 A1 7/2017 Di Padova et al.
2017/0233468 A1 8/2017 Alberici et al.
2018/0194839 A1 7/2018 Padova et al.
2019/0161544 A1 5/2019 Zhang et al.
2019/0194311 A1 6/2019 Fasth et al.
2019/0256588 A1 8/2019 Song et al.

FOREIGN PATENT DOCUMENTS

| CN | 101001645 | A | | 7/2007 | |
|---|---|---|---|---|---|
| CN | 101326195 | A | | 12/2008 | |
| CN | 101646690 | A | | 2/2010 | |
| CN | 102905727 | A | | 1/2013 | |
| CN | 103154031 | A | | 6/2013 | |
| CN | 104936981 | A | * | 9/2015 | ............. A61P 37/00 |
| CN | 105073775 | A | | 11/2015 | |
| CN | 106474470 | A | | 3/2017 | |
| CN | 107488227 | A | | 12/2017 | |
| CN | 107556382 | A | | 1/2018 | |
| CN | 104936981 | B | | 2/2018 | |
| CN | 109206515 | A | | 1/2019 | |
| CN | 109369806 | A | | 2/2019 | |
| CN | 109476733 | A | | 3/2019 | |
| CN | 109796534 | A | | 5/2019 | |
| EP | 3 072 905 | A1 | | 9/2016 | |
| WO | 2009082624 | A2 | | 7/2009 | |
| WO | 2014001368 | A1 | | 1/2014 | |

OTHER PUBLICATIONS

Rudikoff et al., Proc. Natl. Acad. Sci, USA, 1982, vol. 79:1979-1983.*
Rabia et al., Biochem. Eng. J., 2018, vol. 137:365-374.*
Mease et al., Ann. Rheum. Dis., 2017, vol. 76(1): 79-87.*
Glatt Sophie: "Dual IL-17A and IL-17F neutralisation by bimekizumab in psoriatic arthritis: evidence from preclinical experiments and a randomised placebo-controlled clinical trial that IL-17F contributes to human chronic tissue inflammation", Dec. 23, 2017 (Dec. 23, 2017), pp. 523-532, XP055960145, Retrieved from the Internet: URL: https://ard.bmj.com/content/annrheumdi s/77/4/523.full.pdf [retrieved on Sep. 12, 2022].

(Continued)

*Primary Examiner* — Xiaozhen Xie
(74) *Attorney, Agent, or Firm* — Harness, Dickey & Pierce, PLC

(57) ABSTRACT

The present application relates to a method for treating an autoimmune disease by an IL-17 antagonist. The present application relates to an application of an IL-17A binding agent in preparation of a drug for treating an autoimmune disease, such as rheumatoid arthritis, ankylosing spondylitis, and psoriasis, in particular, provides a method for treating inflammation or an autoimmune disease, comprising administering an effective amount of an IL-17 binding agent to a patient, wherein the administration frequency is less than once a week.

18 Claims, No Drawings

Specification includes a Sequence Listing.

(56) References Cited

OTHER PUBLICATIONS

Silfvast-Kaiser Annika et al: "Anti-IL17 therapies for psoriasis", Expert Opinion on Biological Therapy, Informa Healthcare, UK vol. 19, No. 1, Dec. 31, 2018 (Dec. 31, 2018), pp. 45-54, XP009539080, ISSN: 1744-7682, DOI: 10.1080/14712598.2019.1555235, Retrieved from the Internet: URL: https://www.tandfonline.com/doi/full/10.1080/14712598.2019.1555235.

* cited by examiner

SEQUENCE LISTING

```
<160> NUMBER OF SEQ ID NOS: 14

<210> SEQ ID NO 1
<211> LENGTH: 123
<212> TYPE: PRT
<213> ORGANISM: Mus musculus

<400> SEQUENCE: 1

His Val Gln Leu Gln Gln Ser Gly Ala Asp Leu Val Arg Pro Gly Ala
1               5                   10                  15

Ser Val Thr Leu Ser Cys Lys Ala Ser Gly Tyr Ile Phe Thr Asp Tyr
            20                  25                  30

Glu Val His Trp Val Lys Gln Thr Pro Val His Gly Leu Glu Trp Ile
        35                  40                  45

Gly Val Ile Asp Pro Gly Thr Gly Gly Val Ala Tyr Asn Gln Lys Phe
    50                  55                  60
```

-continued

```
Glu Gly Lys Ala Thr Leu Thr Ala Asp Asp Ser Ser Asn Thr Ala Tyr
65                  70                  75                  80

Met Glu Leu Arg Ser Leu Thr Ser Glu Asp Ser Ala Val Tyr Tyr Cys
                85                  90                  95

Thr Arg Tyr Ser Leu Phe Tyr Gly Ser Ser Pro Tyr Ala Met Asp Tyr
            100                 105                 110

Trp Gly Gln Gly Thr Ser Val Thr Val Ser Ser
        115                 120

<210> SEQ ID NO 2
<211> LENGTH: 106
<212> TYPE: PRT
<213> ORGANISM: Mus musculus

<400> SEQUENCE: 2

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Asn Tyr Met
                20                  25                  30

His Trp Phe Gln Gln Lys Pro Gly Thr Ser Pro Lys Leu Trp Ile Tyr
            35                  40                  45

Arg Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Trp Thr
                85                  90                  95

Phe Gly Gly Gly Thr Asn Leu Glu Ile Lys
            100                 105

<210> SEQ ID NO 3
<211> LENGTH: 98
<212> TYPE: PRT
<213> ORGANISM: Homo Sapiens

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg

<210> SEQ ID NO 4
<211> LENGTH: 95
<212> TYPE: PRT
<213> ORGANISM: Homo Sapiens

<400> SEQUENCE: 4

Glu Ile Val Leu Thr Gln Ser Pro Asp Phe Gln Ser Val Thr Pro Lys
1               5                   10                  15
```

-continued

```
Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
            35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro
                85                  90                  95
```

```
<210> SEQ ID NO 5
<211> LENGTH: 123
<212> TYPE: PRT
<213> ORGANISM: Artificial Sequence
<220> FEATURE:
<223> OTHER INFORMATION: Heavy chain variable region

<400> SEQUENCE: 5
```

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Val His Trp Val Arg Gln Ala Pro Gly Gln Gly Leu Glu Trp Met
        35                  40                  45

Gly Val Ile Asp Pro Gly Thr Gly Gly Val Ala Tyr Asn Gln Lys Phe
    50                  55                  60

Glu Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Thr Arg Tyr Ser Leu Phe Tyr Gly Ser Ser Pro Tyr Ala Met Asp Tyr
                100                 105                 110

Trp Gly Gln Gly Thr Leu Val Thr Val Ser Ser
        115                 120
```

```
<210> SEQ ID NO 6
<211> LENGTH: 107
<212> TYPE: PRT
<213> ORGANISM: Artificial Sequence
<220> FEATURE:
<223> OTHER INFORMATION: Light chain variable region

<400> SEQUENCE: 6
```

```
Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Ser Val Asn Tyr Met
            20                  25                  30

His Trp Phe Gln Gln Lys Pro Asp Gln Ser Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Tyr Thr Leu Thr Ile Asn Ser Leu Glu Ala Glu
65                  70                  75                  80

Asp Ala Ala Thr Tyr Tyr Cys Gln Gln Arg Ser Ser Tyr Pro Trp Thr
                85                  90                  95

Phe Gly Gln Gly Thr Lys Leu Glu Ile Lys Arg
```

-continued

```
            100             105
```

<210> SEQ ID NO 7
<211> LENGTH: 5
<212> TYPE: PRT
<213> ORGANISM: Mus musculus

<400> SEQUENCE: 7

Asp Tyr Glu Val His
1               5

<210> SEQ ID NO 8
<211> LENGTH: 17
<212> TYPE: PRT
<213> ORGANISM: Mus musculus

<400> SEQUENCE: 8

Val Ile Asp Pro Gly Thr Gly Gly Val Ala Tyr Asn Gln Lys Phe Glu
1               5                   10                  15

Gly

<210> SEQ ID NO 9
<211> LENGTH: 14
<212> TYPE: PRT
<213> ORGANISM: Mus musculus

<400> SEQUENCE: 9

Tyr Ser Leu Phe Tyr Gly Ser Ser Pro Tyr Ala Met Asp Tyr
1               5                   10

<210> SEQ ID NO 10
<211> LENGTH: 10
<212> TYPE: PRT
<213> ORGANISM: Mus musculus

<400> SEQUENCE: 10

Ser Ala Ser Ser Ser Val Asn Tyr Met His
1               5                   10

<210> SEQ ID NO 11
<211> LENGTH: 7
<212> TYPE: PRT
<213> ORGANISM: Mus musculus

<400> SEQUENCE: 11

Arg Thr Ser Asn Leu Ala Ser
1               5

<210> SEQ ID NO 12
<211> LENGTH: 9
<212> TYPE: PRT
<213> ORGANISM: Mus musculus

<400> SEQUENCE: 12

Gln Gln Arg Ser Ser Tyr Pro Trp Thr
1               5

<210> SEQ ID NO 13
<211> LENGTH: 213
<212> TYPE: PRT
<213> ORGANISM: Artificial Sequence
<220> FEATURE:
<223> OTHER INFORMATION: light chain sequence of the humanized antibody

<400> SEQUENCE: 13

```
Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Ser Val Asn Tyr Met
            20                  25                  30

His Trp Phe Gln Gln Lys Pro Asp Gln Ser Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Tyr Thr Leu Thr Ile Asn Ser Leu Glu Ala Glu
65                  70                  75                  80

Asp Ala Ala Thr Tyr Tyr Cys Gln Gln Arg Ser Ser Tyr Pro Trp Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
    210

<210> SEQ ID NO 14
<211> LENGTH: 453
<212> TYPE: PRT
<213> ORGANISM: Artificial Sequence
<220> FEATURE:
<223> OTHER INFORMATION: heavy chain sequence of the humanized antibody

<400> SEQUENCE: 14

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Val His Trp Val Arg Gln Ala Pro Gly Gln Gly Leu Glu Trp Met
        35                  40                  45

Gly Val Ile Asp Pro Gly Thr Gly Gly Val Ala Tyr Asn Gln Lys Phe
    50                  55                  60

Glu Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Thr Arg Tyr Ser Leu Phe Tyr Gly Ser Ser Pro Tyr Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140
```

-continued

```
Thr Ala Ala Leu Gly Cys Leu Val Lys Asp Tyr Phe Pro Glu Pro Val
145             150             155             160

Thr Val Ser Trp Asn Ser Gly Ala Leu Thr Ser Gly Val His Thr Phe
                165             170             175

Pro Ala Val Leu Gln Ser Ser Gly Leu Tyr Ser Leu Ser Ser Val Val
            180             185             190

Thr Val Pro Ser Ser Ser Leu Gly Thr Gln Thr Tyr Ile Cys Asn Val
            195             200             205

Asn His Lys Pro Ser Asn Thr Lys Val Asp Lys Lys Val Glu Pro Lys
    210             215             220

Ser Cys Asp Lys Thr His Thr Cys Pro Pro Cys Pro Ala Pro Glu Leu
225             230             235             240

Leu Gly Gly Pro Ser Val Phe Leu Phe Pro Pro Lys Pro Lys Asp Thr
            245             250             255

Leu Met Ile Ser Arg Thr Pro Glu Val Thr Cys Val Val Val Asp Val
            260             265             270

Ser His Glu Asp Pro Glu Val Lys Phe Asn Trp Tyr Val Asp Gly Val
        275             280             285

Glu Val His Asn Ala Lys Thr Lys Pro Arg Glu Glu Gln Tyr Asn Ser
    290             295             300

Thr Tyr Arg Val Val Ser Val Leu Thr Val Leu His Gln Asp Trp Leu
305             310             315             320

Asn Gly Lys Glu Tyr Lys Cys Lys Val Ser Asn Lys Ala Leu Pro Ala
            325             330             335

Pro Ile Glu Lys Thr Ile Ser Lys Ala Lys Gly Gln Pro Arg Glu Pro
            340             345             350

Gln Val Tyr Thr Leu Pro Pro Ser Arg Glu Glu Met Thr Lys Asn Gln
        355             360             365

Val Ser Leu Thr Cys Leu Val Lys Gly Phe Tyr Pro Ser Asp Ile Ala
    370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Lys Leu
            405             410             415

Thr Val Asp Lys Ser Arg Trp Gln Gln Gly Asn Val Phe Ser Cys Ser
            420             425             430

Val Met His Glu Ala Leu His Asn His Tyr Thr Gln Lys Ser Leu Ser
    435             440             445

Leu Ser Pro Gly Lys
    450
```

METHOD FOR TREATING AUTOIMMUNE DISEASE BY IL-17 ANTAGONIST

CROSS-REFERENCE TO RELATED APPLICATIONS

The present application is a U.S. National Phase Application under 35 U.S.C. 371 of International Application No. PCT/CN2020/105510, filed on Jul. 29, 2020, which claims priority to China Patent Application No. 201910695261.2 filed on Jul. 30, 2019 and China Patent Application No. 202010523393.X filed on, Jun. 10, 2020, the contents of which are incorporated herein by reference in their entireties.

TECHNICAL FIELD

The present disclosure relates to a method for treating inflammation or autoimmune diseases.

BACKGROUND

The cytokines of the interleukin-17 family, designated interleukin-17A through interleukin-17F, can bind to corresponding receptor members and thereby mediate different inflammatory responses.

The most representative member of this family is interleukin-17A. Lymphocytes that migrate to an infected or injured part of the body secrete interleukin-17A. In one aspect, interleukin-17A induces the expression of inflammatory factors and chemokines, so that more immune cells are recruited to an inflammatory part to intensify the inflammatory response; in another aspect, interleukin-17A also induces the expression of some tissue repair-related factors, thereby accelerating the recovery of the body. Although interleukin-17A serves to augment the immune defense response and protect the body during the host's resistance to infection and tissue repair, it is highly expressed in many patients with autoimmune diseases and tumors, leading to malignant pathological progression since it can induce the expression of many inflammatory factors. Many animal experiments also show that the absence of interleukin-17A or the neutralization of interleukin-17A by antibodies can effectively inhibit the pathological progression of various autoimmune diseases. There is evidence that IL-17 signal-targeting treatment has certain efficacy against autoimmune diseases, including rheumatoid arthritis (RA), psoriasis, axial spondyloarthritis, Crohn's disease, multiple sclerosis (MS), psoriatic disease, asthma, and lupus erythematosus (see, e.g., Aggarwal et al., *J. Leukoc. Biol.*, 71(1):1-8 (2002); Lubberts et al.).

Anti-IL-17A antibodies have been reported in patents such as CN101001645A, CN101326195A and CN101646690A. CN201480003663.7 also discloses an improved antibody effective in reducing or neutralizing IL-17 activity.

There are developed anti-IL-17 drugs, particularly humanized monoclonal antibodies against IL-17 such as Ixekizumab (Eli Lilly), Secukinumab (Novartis) and Brodalumab (SILIQ™), on the market. Secukinumab (Cosentyx®) has been approved by the United States Food and Drug Administration (FDA), the European Medicines Agency (EMA), Japan and Brazil for adult plaque psoriasis, ankylosing spondylitis and psoriatic arthritis. Ixekizumab (Taltz®) has been approved by FDA/EMA for use in treating moderate to severe adult plaque psoriasis. Brodalumab (SILIQ™), an IL-17 receptor monoclonal antibody developed by AstraZeneca/Valeant, has been approved for moderate to severe plaque psoriasis in patients. However, loading therapy (loading) is commonly involved in current treatment regimens with IL-17 drugs.

Therefore, the development of new methods for treating autoimmune diseases is of sufficient interest to pharmaceutical researchers.

CONTENT OF THE PRESENT INVENTION

The present disclosure provides a method for treating inflammation or autoimmune diseases, which comprises administering to a patient an effective amount of an IL-17A binding agent at a frequency of less than once a week.

In some embodiments, the IL-17A binding agent comprises one or more sequences selected from CDR region sequences or amino acid sequences having at least 95% sequence identity therewith:

antibody heavy chain variable region HCDR sequences: amino acid sequences set forth in SEQ ID NOs: 7, 8 and 9; and antibody light chain variable region LCDR sequences: amino acid sequences set forth in SEQ ID NOs: 10, 11 and 12.

In some embodiments, CDR sequences in the light and heavy chains of the IL-17A antibody are shown in the table below:

|  |  | mAb049 |  |
| --- | --- | --- | --- |
| | Domain | Sequences | SEQ ID NO |
| VH | CDR1 | DYEVH | 7 |
| | CDR2 | VIDPGTGGVAYNQKFEG | 8 |
| | CDR3 | YSLFYGSSPYAMDY | 9 |
| VL | CDR1 | SASSSVNYMH | 10 |
| | CDR2 | RTSNLAS | 11 |
| | CDR3 | QQRSSYPWT | 12 |

Preferably, in some embodiments, the IL-17A antibody or an antigen-binding fragment thereof is selected from a murine antibody, a chimeric antibody, a recombinant antibody of a humanized antibody or an antigen-binding fragment thereof.

Further, light chain FR and heavy chain FR sequences of the light chain variable region and heavy chain variable region of humanized antibody are derived from a human germline light chain and a human germline heavy chain or mutant sequences thereof, respectively.

In optional embodiments, the IL-17A antibody comprises a heavy chain variable region set forth in SEQ ID NO: 3 or a variant thereof, wherein the variant preferably has 0-10 amino acid variations in the heavy chain variable region sequence set forth in SEQ ID NO: 3, the amino acid variations are more preferably A93T and T71A amino acid reverse mutations; the IL-17A antibody comprises a light chain variable region set forth in SEQ ID NO: 4 or a variant thereof, wherein the variant preferably has a sequence with 0-10 amino acid variations in the light chain variable region set forth in SEQ ID NO: 4, the amino acid variations are more preferably F71Y, K49Y, Y36F and L47W amino acid reverse mutations.

Heavy chain variable region (VH1-18)

SEQ ID NO: 3

QVQLVQSGAEVKKPGASVKVSCKASGYTFTSYGISWVRQAPGQGLEWMGWI

SAYNGNTNYAQKLQGRVTMTTDTSTSTAYMELRSLRSDDTAVYYCAR

-continued

Light chain variable region (A10)
```
                                          SEQ ID NO: 4
EIVLTQSPDFQSVTPKEKVTITCRASQSIGSSLHWYQQKPDQSPKLLIKYA

SQSFSGVPSRFSGSGSGTDFTLTINSLEAEDAATYYCHQSSSLP
```

Further, the heavy chain variable region or the light chain variable region of the aforementioned IL-17A antibody sequence is as follows:

Heavy chain variable region
```
                                          SEQ ID NO: 5
EVQLVQSGAEVKKPGASVKVSCKASGYTFTDYEVHWVRQAPGQGLEWMGVI

DPGTGGVAYNQKFEGRVTMTADTSTSTAYMELRSLRSDDTAVYYCTRYSLF

YGSSPYAMDYWGQGTLVTVSS
```

Light chain variable region
```
                                          SEQ ID NO: 6
EIVLTQSPDFQSVTPKEKVTITCSASSSVNYMHWFQQKPDQSPKLWIYRTS

NLASGVPSRFSGSGSGTDYTLTINSLEAEDAATYYCQQRSSYPWTFGQGTK

LEIKR
```

An immunoglobulin may be derived from any commonly known isotype and includes, but is not limited to, IgA, secretory IgA, IgG, and IgM. An IgG subclass is also well known to those skilled in the art and includes, but is not limited to, IgG1, IgG2, IgG3, and IgG4. "Isotype" refers to an Ab class or subclass encoded by a heavy chain constant region gene (e.g., IgM or IgG1). In some optional embodiments, the IL-17A antibody described herein comprises a heavy chain constant region of human IgG1, IgG2, IgG3, or IgG4 isotype, preferably a heavy chain constant region of IgG1 isotype.

In other optional embodiments, the anti-IL-17A antibody or the antigen-binding fragment thereof comprises a κ or λ light chain constant region.

In some embodiments, the light chain sequence of the humanized antibody is a sequence set forth in SEQ ID NO: 13, and the heavy chain sequence is a sequence set forth in SEQ ID NO. 14.

Light chain
```
                                          SEQ ID NO: 13
EIVLTQSPDFQSVTPKEKVTITCSASSSVNYMHWFQQKPDQSPKLWIYRTS

NLASGVPSRFSGSGSGTDYTLTINSLEAEDAATYYCQQRSSYPWTFGQGTK

LEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPV

TKSFNRGEC
```

Heavy chain
```
                                          SEQ ID NO: 14
EVQLVQSGAEVKKPGASVKVSCKASGYTFTDYEVHWVRQAPGQGLEWMGVI

DPGTGGVAYNQKFEGRVTMTADTSTSTAYMELRSLRSDDTAVYYCTRYSLF

YGSSPYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNSTY
```

-continued
```
RVVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSDG

SFFLYSKLTVDKSRWQQGNVFSCSVMHEALHNHYTQKSLSLSPGK
```

In addition, the IL-17A antibody described herein has the characteristics of high affinity, rapid onset of action, low toxicity and the like, and thus can be used for treating inflammation or autoimmune diseases at low dose and low frequency.

According to the type and severity of the disease, the weight of the patient, and the tolerance of the patient to the drug, the IL-17A binding agent described herein is administered at a dose of 40-300 mg, and, in embodiments, may be administered at a dose of 40 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg or 300 mg, preferably 80 mg, 120 mg, 160 mg, 200 mg or 240 mg.

Methods of treating inflammation or autoimmune diseases include a loading regimen in which an IL-17A antibody can be administered at low dose or high dose for treatment and then administered for maintenance therapy when response or partial response occurs in a patient. For example, the administration regimen for treating moderate to severe plaque psoriasis with Secukinumab of Novartis is as follows: subcutaneous injection of 150 mg every week, for a total of 5 injections (at weeks 0, 1, 2, 3 and 4), followed by subcutaneous injection of Secukinumab at a dose of 150 mg every 4 weeks for maintenance therapy. The administration regimen for treating moderate to severe plaque psoriasis with Ixekizumab of Eli Lilly is as follows: a dose of 160 mg for the first administration, then subcutaneous injection at a dose of 80 mg every 2 weeks, for a total of 5 injections, followed by administration at a dose of 80 mg every 4 weeks for maintenance therapy. The administration regimen as a whole is complicated, virtually increasing the treatment burden on patients and thus leading to low patient compliance with the treatment. The treatment regimen of the present disclosure does not include a loading regimen and thus is simple, with a low probability of missed administration. Besides, the treatment regimen without a loading regimen can effectively reduce the treatment burden on patients and thus improve the patient compliance with the treatment.

Some embodiments provide methods for treating inflammation or autoimmune diseases without a loading regimen (loading). The loading regimen (loading) refers to a regimen in which IL-17A antibody is administered at high frequency (relative to the administration frequency for maintenance therapy) in the initial stage of treatment to treat inflammation or autoimmune diseases. The administration at high frequency may be administration at a frequency of once a week starting at week zero, or once every 2 weeks starting at week zero, or once every 3 weeks starting at week zero, or once every 4 weeks starting at week zero, or once every 6 weeks starting at week zero, or once every 8 weeks starting at week zero, or at a frequency with longer time intervals.

Further, in the loading regimen described herein, administration is performed at least one or more times, including but not limited to 1, 2, 3, 4, 5, or more times.

In some embodiments, in the loading regimen, the administration is performed at a frequency of once a week starting at week zero, for a total of 3 administrations.

In some embodiments, in the loading regimen, the administration is performed at a frequency of once a week starting at week zero, for a total of 4 administrations.

In some embodiments, in the loading regimen, the administration is performed at a frequency of once a week starting at week zero, for a total of 5 administrations.

In some embodiments, in the loading regimen, the administration is performed at a frequency of once every 2 weeks starting at week zero, for a total of 3 administrations.

In some embodiments, in the loading regimen, the administration is performed at a frequency of once every 2 weeks starting at week zero, for a total of 4 administrations.

In some embodiments, in the loading regimen, the administration is performed at a frequency of once every 2 weeks starting at week zero, for a total of 5 administrations.

In some embodiments, in the loading regimen, the administration is performed at a frequency of once every 3 weeks starting at week zero, for a total of 3 administrations.

In some embodiments, in the loading regimen, the administration is performed at a frequency of once every 3 weeks starting at week zero, for a total of 4 administrations.

In some embodiments, in the loading regimen, the administration is performed at a frequency of once every 3 weeks starting at week zero, for a total of 5 administrations.

In some embodiments, in the loading regimen, the administration is performed at a frequency of once every 4 weeks starting at week zero, for a total of 3 administrations.

In some embodiments, in the loading regimen, the administration is performed at a frequency of once every 4 weeks starting at week zero, for a total of 4 administrations.

In some embodiments, in the loading regimen, the administration is performed at a frequency of once every 4 weeks starting at week zero, for a total of 5 administrations.

The units "month" and "week" of the administration cycle of the present disclosure may be appropriately converted in some cases, and typically 4 weeks are counted as 1 month.

Further, in some embodiments, the method for treating inflammation or autoimmune diseases does not include a loading regimen comprising e.g., administering to the patient the aforementioned IL-17A binding agent at a dose of 40-300 mg (e.g., 80 mg, 120 mg, 160 mg, 200 mg, or 240 mg) weekly starting at week zero (e.g., administration at weeks 0/1/2/3 or weeks 0/1/2/3/4/5).

In some embodiments, the method for treating inflammation or autoimmune diseases does not include a loading regimen comprising, e.g., administering to the patient the aforementioned IL-17A binding agent at a dose of 40-300 mg (e.g., 80 mg, 120 mg, 160 mg, 200 mg, or 240 mg) every 2 weeks starting at week zero (e.g., administration at weeks 0/2 or weeks 0/2/4).

In some embodiments, the method for treating inflammation or autoimmune diseases does not include a loading regimen comprising, e.g., administering to the patient the aforementioned IL-17A binding agent at a dose of 40-300 mg (e.g., 80 mg, 120 mg, 160 mg, 200 mg, or 240 mg) every 3 weeks starting at week zero (e.g., administration at weeks 0/3 or weeks 0/3/6).

In some embodiments, the method for treating inflammation or autoimmune diseases does not include a loading regimen comprising, e.g., administering to the patient the aforementioned IL-17A binding agent at a dose of 40-300 mg (e.g., 80 mg, 120 mg, 160 mg, 200 mg, or 240 mg) every 4 weeks starting at week zero (e.g., administration at weeks 0/4 or weeks 0/4/8).

In another aspect, in some embodiments, the method for treating inflammation or autoimmune diseases comprises administering to a patient the IL-17A binding agent at a dose of 40-300 mg (e.g., 80 mg, 120 mg, 160 mg, 200 mg, or 240 mg) and a frequency of once every three weeks.

In some embodiments, the method for treating inflammation or autoimmune diseases comprises administering to a patient the IL-17A binding agent at a dose of 40-300 mg (e.g., 80 mg, 120 mg, 160 mg, 200 mg, or 240 mg) and a frequency of once every four weeks.

In some embodiments, the method for treating inflammation or autoimmune diseases comprises administering to a patient the IL-17A binding agent at a dose of 40-300 mg (e.g., 80 mg, 120 mg, 160 mg, 200 mg, or 240 mg) and a frequency of once every five weeks.

In some embodiments, the method for treating inflammation or autoimmune diseases comprises administering to a patient the IL-17A binding agent at a dose of 40-300 mg (e.g., 80 mg, 120 mg, 160 mg, 200 mg, or 240 mg) and a frequency of once every six weeks.

In some embodiments, the method for treating inflammation or autoimmune diseases comprises administering to a patient the IL-17A binding agent at a dose of 40-300 mg (e.g., 80 mg, 120 mg, 160 mg, 200 mg, or 240 mg) and a frequency of once every seven weeks.

In some embodiments, the method for treating inflammation or autoimmune diseases comprises administering to a patient the IL-17A binding agent at a dose of 40-300 mg (e.g., 80 mg, 120 mg, 160 mg, 200 mg, or 240 mg) and a frequency of once every eight weeks.

In some embodiments, the method for treating inflammation or autoimmune diseases comprises administering to a patient the IL-17A binding agent at a dose of 40-300 mg (e.g., 80 mg, 120 mg, 160 mg, 200 mg, or 240 mg) and a frequency of once every ten weeks.

In some embodiments, the method for treating inflammation or autoimmune diseases comprises administering to a patient the IL-17A binding agent at a dose of 40-300 mg (e.g., 80 mg, 120 mg, 160 mg, 200 mg, or 240 mg) and a frequency of once every twelve weeks.

The embodiments of the present disclosure provide methods for treating inflammation or autoimmune diseases comprising before administering to a patient the IL-17A binding agent at a dose of 40-300 mg, not treating the patient with an loading regimen (loading), in which the administration may be performed at a frequency of once a week starting at week zero, or once every 2 weeks starting at week zero, or once every 3 weeks starting at week zero, or once every 4 weeks starting at week zero, or once every 6 weeks starting at week zero, or once every 8 weeks starting at week zero, or at a frequency with longer time intervals, for a total of at least one or more administrations, including but not limited to 1, 2, 3, 4, 5 or more administrations.

Further, the method for treating inflammation or autoimmune diseases disclosed herein comprises before administering to a patient the IL-17A binding agent at a dose of 40-300 mg, not treating the patient with a loading regimen (loading) comprising, e.g., administering to the patient the aforementioned IL-17A binding agent at a dose of 40-300 mg (e.g., 20 mg, 60 mg, 80 mg, 120 mg, 160 mg, 200 mg, or 240 mg) weekly starting at week zero (e.g., weeks 0/1/2/3 or weeks 0/1/2/3/4/5).

The method for treating inflammation or autoimmune diseases disclosed herein comprises before administering to a patient the IL-17A binding agent at a dose of 40-300 mg, not treating the patient with a loading regimen (loading) comprising, e.g., administering to the patient the aforementioned IL-17A binding agent at a dose of 40-300 mg (e.g., 20 mg, 60 mg, 80 mg, 120 mg, 160 mg, 200 mg, or 240 mg) every 2 weeks starting at week zero (e.g., weeks 0/2 or weeks 0/2/4).

The method for treating inflammation or autoimmune diseases disclosed herein comprises before administering to a patient the IL-17A binding agent at a dose of 40-300 mg, not treating the patient with a loading regimen (loading) comprising, e.g., administering to the patient the aforementioned IL-17A binding agent at a dose of 40-300 mg (e.g., 20 mg, 60 mg, 80 mg, 120 mg, 160 mg, 200 mg, or 240 mg) every 3 weeks starting at week zero (e.g., weeks 0/3 or weeks 0/3/6).

The method for treating inflammation or autoimmune diseases disclosed herein comprises before administering to a patient the IL-17A binding agent at a dose of 40-300 mg, not treating the patient with a loading regimen (loading) comprising, e.g., administering to the patient the aforementioned IL-17A binding agent at a dose of 40-300 mg (e.g., 20 mg, 60 mg, 80 mg, 120 mg, 160 mg, 200 mg, or 240 mg) every 4 weeks starting at week zero (e.g., weeks 0/4 or weeks 0/4/8).

In the method for treating inflammation or autoimmune diseases disclosed herein, the patient has moderate to severe active ankylosing spondylitis.

In some embodiments, the patient is one who has previously been inadequately responsive to treatment with at least one nonsteroidal anti-inflammatory drug (NSAID) (e.g., aspirin, ibuprofen, acetaminophen, indomethacin, naproxen, nabumetone, diclofenac, nimesulide, rofecoxib or celecoxib).

In other embodiments, the treatment method disclosed herein comprises after administering to a patient with moderate to severe active ankylosing spondylitis the IL-17A binding agent at a dose of 40-300 mg, further administering to the patient an NSAID, methotrexate, sulfasalazine, or prednisolone.

In other embodiments, in the method for treating inflammation or autoimmune diseases disclosed herein, the patient has active psoriatic arthritis, preferably co-existing psoriasis.

In certain embodiments, the patient is a TNFi failure or a methotrexate (DMARD) failure.

In certain embodiments, the treatment method disclosed herein comprises after administering to a patient with active psoriatic arthritis the IL-17A binding agent at a dose of 40-300 mg, further administering to the patient methotrexate.

In another aspect, in the method for treating inflammation or autoimmune diseases disclosed herein, the patient has plaque psoriasis, preferably moderate to severe plaque psoriasis.

In some embodiments, the treatment method disclosed herein comprises before administering to a patient with plaque psoriasis the IL-17A binding agent at a dose of 40-300 mg, not treating the patient with a systemic therapeutic agent for psoriasis.

In some embodiments, the treatment method disclosed herein comprises before administering to a patient with plaque psoriasis the IL-17A binding agent at a dose of 40-300 mg, treating the patient with a systemic therapeutic agent for psoriasis.

The systemic treatment in the present disclosure is selected from methotrexate, cyclosporine, fumarate, acitretin, alefacept, adalimumab, efalizumab, etanercept, infliximab, golimumab and Ustekinumab, preferably methotrexate.

The present disclosure provides use of the IL-17A antibody in preparing a medicament for treating inflammation or autoimmune diseases, wherein the medicament is formulated and stored in a container so as to allow for administration of an effective amount of IL-17A to a patient with an inflammation or autoimmune disease.

The present disclosure also provides a method for treating inflammation or autoimmune diseases, which comprises administering to a patient an effective amount of an IL-17A binding agent at a frequency of once every 5-8 weeks (e.g., once every five weeks, once every six weeks, once every seven weeks or once every eight weeks).

Further, in optional embodiments, the treatment method disclosed herein in which administration is performed at a frequency of once every 5-8 weeks may comprise or may not comprise a loading regimen (loading).

In some embodiments, the treatment method disclosed herein in which administration is performed at a frequency of once every 5-8 weeks includes a loading regimen (loading) comprising, e.g., administering to the patient the aforementioned IL-17A binding agent at a dose of 40-300 mg (e.g., 80 mg, 120 mg, 160 mg, 200 mg, or 240 mg) weekly starting at week zero (e.g., administration at weeks 0/1/2/3 or weeks 0/1/2/3/4/5), every 2 weeks (e.g., administration at weeks 0/2 or weeks 0/2/4), every 3 weeks or every 4 weeks.

Still further, in optional embodiments, the loading regimen may last for a period of 6 weeks, 7 weeks, 8 weeks, 9 weeks, 10 weeks, 11 weeks, 12 weeks, 13 weeks, 14 weeks or 15 weeks.

The inflammation or autoimmune disease in the present disclosure is selected from inflammation or autoimmune diseases; the disease is preferably psoriasis, psoriatic arthritis, ankylosing spondylitis, multiple sclerosis, or inflammatory arthritis.

The treatment cycle of the treatment method disclosed herein is 20 weeks.

The route of administration described herein may be oral administration, parenteral administration, or transdermal administration, the parenteral administration including but not limited to intravenous injection, subcutaneous injection, and intramuscular injection, preferably subcutaneous injection.

In some embodiments of the present disclosure, the IL-17A antibody is administered by injection, e.g., subcutaneous or intravenous injection, prior to which the IL-17A antibody is necessarily formulated into an injectable form. Particularly preferred injectable forms of the IL-17A antibody are injections or lyophilized powder for injection comprising the IL-17A antibody, a buffer, a stabilizer, and an optional surfactant. The buffer is a histidine-hydrochloride system; the stabilizer may be selected from sugars and amino acids, preferably disaccharides, such as sucrose, lactose, trehalose, and maltose. The surfactant is selected from polyoxyethylene hydrogenated castor oil, glycerol fatty acid esters, and polyoxyethylene sorbitan fatty acid esters, preferably, the polyoxyethylene sorbitan fatty acid ester being polysorbate 20, 40, 60 or 80, most preferably polysorbate 20. The most preferred injectable form of the IL-17A antibody comprises the IL-17A antibody, histidine hydrochloride buffer, sucrose and polysorbate 80.

Unless otherwise explained, terms in the present disclosure have the following meanings:

The "binding agent" described herein refers to a soluble receptor or a fragment thereof or an analog thereof, or an antibody or a fragment thereof or an analog thereof, capable of binding to a target. The "IL-17A binding agent" described herein refers to an antibody or a fragment thereof or an analog thereof capable of specifically recognizing IL-17A and binding to IL-17A.

The term "IL-17A" refers generally to native or recombinant human IL-17A, as well as a non-human homolog of human IL-17A. Unless otherwise indicated, the molar concentration of IL-17A is calculated using the molecular weight of the homodimer of IL-17A (e.g., 30 KDa for human IL-17A).

The antibody described herein refers to an immunoglobulin, which is of a tetrapeptide chain structure formed by connection between two identical heavy chains and two identical light chains by interchain disulfide bonds. Immunoglobulins differ in amino acid composition and arrangement of their heavy chain constant regions and therefore in their antigenicity. Accordingly, immunoglobulins can be classified into five classes, or isotypes of the immunoglobulins, namely IgM, IgD, IgG, IgA, and IgE. The Ig of the same class can be divided into different subclasses according to the differences of amino acid composition of the hinge regions and the number and position of disulfide bonds of the heavy chains; for example, IgG can be divided into IgG1, IgG2, IgG3, and IgG4. Light chains are classified into κ or λ chains by the differences in the constant regions.

The sequences of about 110 amino acids of the antibody heavy and light chains near the N-terminus vary considerably and thus are referred to as variable regions (V regions); the remaining amino acid sequences near the C-terminus are relatively stable and thus are referred to as constant regions (C regions). The variable regions comprise 3 hypervariable regions (HVRs) and 4 framework regions (FRs) with relatively conservative sequences. The 3 hypervariable regions determine the specificity of the antibody and thus are also known as complementarity determining regions (CDRs). Each light chain variable region (VL) or heavy chain variable region (VH) consists of 3 CDR regions and 4 FR regions arranged from the amino-terminus to the carboxy-terminus in the following order: FR1, CDR1, FR2, CDR2, FR3, CDR3, and FR4. The 3 CDR regions of the light chain refer to LCDR1, LCDR2, and LCDR3; the 3 CDR regions of the heavy chain refer to HCDR1, HCDR2 and HCDR3.

The "antigen-binding fragment" described herein refers to an Fab fragment, an Fab' fragment, an F(ab')2 fragment, or a single Fv fragment having antigen-binding activity. Fv antibodies are the smallest antibody fragments that contain the variable regions of the heavy and light chains, but no constant regions, of antibodies, and have all the antigen-binding sites. In general, an Fv antibody also comprises a polypeptide linker between the VH and VL domains that is capable of forming the structure required for antigen binding.

The "humanized antibody" described herein, also referred to as CDR-grafted antibody, refers to an antibody produced by grafting mouse CDR sequences into a human antibody variable region framework, i.e., a different type of human germline antibody framework sequence. Therefore, the strong antibody variable antibody reaction induced by a large amount of mouse protein components contained in the chimeric antibody can be overcome. Such framework sequences can be obtained from public DNA databases or disclosed references that include germline antibody gene sequences. For example, germline DNA sequences of genes of the human heavy and light chain variable regions can be found in the "VBase" human germline sequence database (available at the Internet address www.mrccpe.com.ac.uk/vbase), as well as in Kabat, E. A. et al., 1991 *Sequences of Proteins of Immunological Interest,* 5th edition.

The "murine antibody" described herein is a monoclonal antibody against human TIM-3 prepared according to the knowledge and skill in the art. At the time of preparation, TIM-3 antigen is injected into test subjects, and then hybridomas expressing an antibody with the desired sequence or functional properties are isolated. In one preferred embodiment of the present disclosure, the murine TIM-3 antibody or the antigen-binding fragment thereof may further comprise a light chain constant region of a murine κ or λ chain or a variant thereof, or further comprise a heavy chain constant region of a murine IgG1, IgG2, or IgG3 or a variant thereof.

The "chimeric antibody" described herein refers to an antibody obtained by fusing a variable region of a murine antibody and a constant region of a human antibody, which can reduce an immune response induced by the murine antibody. The chimeric antibody is established by firstly establishing hybridoma secreting murine specific monoclonal antibody, then cloning a variable region gene from the mouse hybridoma cells, cloning a constant region gene of human antibody as required, connecting the mouse variable region gene and the human constant region gene into a chimeric gene, inserting the chimeric gene into an expression vector, and finally expressing chimeric antibody molecules in a eukaryotic system or prokaryotic system.

The heavy or light chain variable region sequence in the IL-17A antibody sequence described herein is analyzed using the Molecular Operating Environment (MOE) database software and translated into an amino acid sequence. In another aspect, the heavy or light chain variable region sequence in the IL-17A antibody sequence can also be analyzed using database software such as IMGT/Domain-GapAlign and translated into an amino acid sequence (see *J. Methods Mol Biol,* 2012, 882, 605-633). However, when database software such as MOE or IMGT is used to provide antibody sequences or structures, it should be noted that different databases encode or resolve the same antibody sequence differently.

The "effective amount or effective dose" described herein includes an amount sufficient to ameliorate or prevent a symptom or condition of a medical condition. The effective amount or effective dose also means an amount sufficient to allow or facilitate diagnosis. The effective amount for a particular patient or veterinary subject may vary depending on factors such as the condition to be treated, the general health of the patient, the route and dose of administration and the severity of side effects. The effective amount or dose can be the maximum dose or administration regimen that avoids significant side effects or toxic effects.

"Treating" or "treatment" means administering a therapeutic agent, such as a composition comprising any one of the binding agents of the present disclosure, either internally or externally to a patient with one or more symptoms of a disease on which the therapeutic agent is known to have a therapeutic effect. Typically, the therapeutic agent is administered in an amount effective in alleviating one or more symptoms of the disease in the patient or population being treated, whether by inducing regression of such symptoms or inhibiting the development of such symptoms to any clinically measurable degree. The amount of therapeutic agent effective in alleviating the symptoms of any particular disease (also referred to as a "therapeutically effective amount") may vary depending on a variety of factors, such as the disease state, age, and weight of the patient, and the ability of the drug to produce a desired therapeutic effect in the patient.

The term "antigen-binding fragment" of an antibody refers to an antibody fragment that retains the ability to specifically bind to an antigen (e.g., IL-17). It has been shown that the antigen-binding function of an antibody can be performed by fragments of a full-length antibody. Examples of binding fragments encompassed within the term "antigen-binding portion" of an antibody include Fab fragments, which are monovalent fragments consisting of VL, VH, CL and CH1 domains; F(ab')2 fragments, which are bivalent fragments comprising two Fab fragments linked by a disulfide bridge in the hinge regions; Fd fragments consisting of VH and CH1 domains; Fv fragments consisting of the VL and VH domains of a single arm of an antibody; dAb fragments (Ward et al., 1989, *Nature*, 341: 544-546), which consist of VH domains; and isolated complementarity determining regions (CDRs).

Herein are described 4 variants of the human IL-17A protein:

1) The terms "human IL-17A (huIL-17A)" and "native human IL-17A" used herein refer to human IL-17A proteins in the mature forms under accession Nos. NP-002181 and AAT22064 (i.e., residues 24-155), as well as native variants and polymorphisms thereof.

2) The term "rhIL-17A" used herein refers to recombinant human IL-17A. This nomenclature is used to indicate IL-17A in various forms, and the usage may not match that in the literature.

3) The term "His-huIL-17A" used herein refers to recombinant human IL-17A with a His tag attached to the N-terminus. FLAG-huIL-17A refers to recombinant human IL-17A with a Flag tag attached to the N-terminus. In some experiments, FLAG-huIL-17A is biotinylated.

4) R&D Systems human IL-17A described herein refers to recombinant human IL-17A purchased from R&D Systems.

The term "optional" or "optionally" means that the event or circumstance subsequently described may, but not necessarily, occur, and that the description includes instances where the event or circumstance occurs or does not occur. For example, "optionally comprising 1-3 antibody heavy chain variable regions" means that the antibody heavy chain variable region of a particular sequence may, but not necessarily, be present, and may be, if present, in an amount of 1, 2 or 3.

The step of transforming host cells with recombinant DNA described herein can be performed using conventional techniques well known to those skilled in the art. The obtained transformants can be cultivated by conventional methods to express the antibody encoded by the genes of the present disclosure. The medium is selected from various conventional media depending on the host cells used, and the host cells are incubated under conditions appropriate for their growth.

The engineered antibody or the antigen-binding fragment of the present disclosure can be prepared and purified using conventional methods. For example, cDNA sequences encoding the heavy and light chains can be cloned and recombined into a GS expression vector. Recombinant immunoglobulin expression vectors can be stably transfected into CHO cells. As a more recommended prior art, mammalian expression systems will result in glycosylation of the antibody, particularly at the highly conservative N-terminal site of the Fc region. Stable clones are obtained by expression of the antibody that specifically bind to human TIM-3. Positive clones are expanded in serum-free medium in bioreactor to produce the antibody. The culture with the secreted antibody can be purified using conventional techniques. For example, purification is carried out on an A or G Sepharose FF column containing an adjusted buffer. Non-specifically bound fractions are washed away. The bound antibody is eluted using pH gradient method, and the antibody fragments are detected by SDS-PAGE and collected. The antibody can be filtered and concentrated using conventional methods. Soluble mixtures and polymers can also be removed using conventional methods, such as molecular sieves and ion exchange. The resulting product needs to be immediately frozen, e.g., at −70° C., or lyophilized.

"Affinity" refers to the degree of interaction between an antibody and an antigen at a single antigen site. Within the antigen sites, the variable regions on the antibody "arms" interact with the antigens at numerous sites via weak non-covalent forces. The more the interactions, the higher the affinity.

The "homology" described herein refers to sequence similarity between two polynucleotide sequences or between two polypeptides. When positions in two compared sequences are all occupied by the same base or amino acid monomer subunit, for example, if a position in each of two DNA molecules is occupied by adenine, the molecules are homologous at that position. The homology percentage between two sequences is a function of the number of matched or homologous positions shared by the two sequences divided by the number of the compared positions×100%. For example, in best alignment of sequences, if 6 out of 10 positions in two sequences match or are homologous, the two sequences are 60% homologous; if 95 out of 100 positions in two sequences match or are homologous, the two sequences are 95% homologous. In general, the comparison is made when two aligned sequences give the greatest homology percentage.

Reference may be made to the following definitions: the Committee for Medicinal Products for Human Use (CHMP) of the European Medicines Agency for the Evaluation of Medicines for Human Use, Guideline on Clinical Investigation of Medicinal Products Indicated for the Treatment of Psoriasis (2004), CHMP/EWP/2454/02 corr document (London, UK): response to treatment (responder): patients who achieve 75% improvement (reduction) in Psoriasis Area And Severity Index (PAST) score (also referred to as PASI75) compared to baseline are defined as responders.

Partial response (partial responder): patients who archive 50% improvement (also referred to as PASI50) but less than 75% improvement (also referred to as PASI75) in PASI score from baseline are defined as partial responders.

Non-response (non-responder): patients who achieve <50% reduction in PASI score from baseline are defined as non-responders.

Relapse (relapser): when the previously achieved improvement in PASI in the study is reduced by 50%, the patients are considered as "relapsers".

Rebound (rebounder): deterioration over PASI baseline value or worsening of skin lesions of psoriasis within 8 weeks of stopping therapy, e.g., PASI >125% of PASI baseline value.

In the PASI scoring system, erythema, thickening (plaque elevation and hardening), and scaling (desquamation) over the head, trunk, and upper and lower extremities are assessed as defined in Table 1. A score of 0 to 4 is given to the average severity of each symptom in each of the four body regions. The area covered by the lesions in each body region is assessed as a percentage to the total area of that particular body region. As the head, upper extremities, trunk, and lower extremities correspond to approximately 10%, 20%, 30%, and 40% of body surface area, respectively, the PASI score is calculated by the formula:

$$PASI=0.1(EH+IH+DH)AH+0.2(EU+IU+DU)AU+0.3$$
$$(ET+IT+DT)AT+0.4(EL+IL+DL)AL$$

The PASI score may range from a low value of 0 (corresponding to no symptom of psoriasis) to a theoretical maximum of 72.0. The PASI score is accurate to one tenth, e.g., 9.0, 10.1, 14.2, 17.3, etc. Further information on PASI scoring can be obtained from Henseler T, Schmitt-Rau K (2008) *Int. J. Dermatol.*; 47:1019-1023, or see relevant contents in CN10315403 or U.S. Pat. No. 9,717,791, which are incorporated herein by reference for illustration.

DETAILED DESCRIPTION OF THE PREFERRED EMBODIMENT

The following examples further illustrate the present disclosure, but the present disclosure is not limited thereto.

Example 1

1. Test Antibody and Compound

IL-17A antibody, the heavy and light chain sequences being set forth in SEQ ID NO: 13 and SEQ ID NO: 14 as disclosed herein, 200 mg/piece, 80 mg/mL prepared as a standby.

2. Enrollment Criteria (1) Patients diagnosed with at least 6 months of chronic plaque psoriasis by examination.

(2) Subjects are candidates for systemic treatment/photo-therapy/chemical phototherapy.

(3) Moderate to severe plaque psoriasis, defined as follows:

a PASI score of 12 or greater, and a PGA score of 3 or greater, and

10% BSA involvement or greater by plaque psoriasis.

3. Grouping

Patients meeting the enrollment criteria were randomized into groups according to the order of screening numbers in a ratio of 1:1:1:1:1:1.

4. Therapeutic Regimen

Regimen 1: IL-17A antibody, fixed dose of 40 mg, sub-cutaneous injection, once every 4 weeks;

Regimen 2: IL-17A antibody, fixed dose of 80 mg, sub-cutaneous injection, once every 4 weeks;

Regimen 3: IL-17A antibody, fixed dose of 160 mg, subcutaneous injection, once every 4 weeks;

Regimen 4: IL-17A antibody, fixed dose of 240 mg, subcutaneous injection, once every 4 weeks;

Regimen 5: IL-17A antibody, fixed dose of 240 mg, subcutaneous injection, once every 8 weeks;

Placebo group: do not receive any positive treatment.

5. Results 187 subjects were randomized to receive IL-17A antibody at a dose of 40 mg (37 subjects), 80 mg (38 subjects), 160 mg (38 subjects), or 240 mg (37 subjects) or a placebo (37 subjects). The percentage reduction in PAST scores from baseline was greatly improved in all the groups of patients relative to the placebo group. At week 12, PAST 75 response rates were significantly higher in all the groups (40 mg, 80 mg, 160 mg, 240 mg: 56.8%, 65.8%, 81.6%, 89.2%; $p<0.001$ (calculated using chi-squared test)) than those in the placebo group (5.4%). At week 12, PAST 90 response rates were significantly higher in all the groups (40 mg, 80 mg, 160 mg, 240 mg: 29.7%, 36.8%, 55.3%, 64.9%; $p<0.001$ (calculated using chi-squared test)) than those in the placebo group (5.4%).

In addition, at week 12, PGA0/1 was significantly higher in all the groups (40 mg, 80 mg, 160 mg, 240 mg: 45.9%, 47.4%, 60.5%, 73%) than that in the placebo group (8.1%).

The most common treatment emergent adverse events (TEAEs) included upper respiratory infection (treatment group, 13.3% vs. placebo, 16.2%) and hyperuricemia (treatment group, 7.3% vs. placebo, 5.4%). Treatment-related TEAEs were observed in 65 cases from the treatment groups (43.3%) and 11 cases from the placebo group (29.7%). TEAEs were mostly mild or moderate. Severe TEAEs occurred in 1 subject from the treatment groups (0.7%) and 2 subjects from the placebo group (5.4%), and were all considered independent of the drug. 1 subject from the treatment groups (0.7%), and 1 subject from the placebo group (2.7%) discontinued treatment due to TEAEs. No mortality was reported.

The IL-17A antibody of the present disclosure showed better efficacy in patients with moderate to severe plaque psoriasis in comparison with the placebo. At week 12, the number of PASI75 responders was higher at the dose of 240 mg than at the other doses. The IL-17A antibody of the present disclosure was well tolerated in this trial.

What is claimed is:

1. A method for treating an inflammatory or autoimmune disease involving an IL-17A-mediated inflammatory response, comprising administering to a patient in need thereof an IL-17A binding agent at a dose of 40-300 mg with a frequency selected from once every four weeks and once every eight weeks, wherein the IL-17A binding agent comprises a heavy chain variable region and a light chain variable region, and the heavy chain variable region comprises HCDR1, HCDR2 and HCDR3 set forth in SEQ ID NOs: 7, 8 and 9, respectively; and the light chain variable region comprises LCDR1, LCDR2 and LCDR3 set forth in SEQ ID NOs: 10, 11 and 12, respectively.

2. The method according to claim 1, wherein the IL-17A binding agent is administered at a frequency of once every four weeks.

3. The method according to claim 1, wherein the IL-17A binding agent is administered at a dose of 80 mg, 120 mg, 160 mg, 200 mg or 240 mg.

4. The method according to claim 1, wherein the administration is performed orally, intravenously, or subcutaneously.

5. The method according to claim 1, wherein the method does not include a loading regimen, in which the IL-17A binding agent is administered at a frequency higher than once every four weeks in the initial stage of treatment.

6. The method according to claim 1, wherein the inflammatory or autoimmune disease is selected from psoriasis, psoriatic arthritis, ankylosing spondylitis, multiple sclerosis and inflammatory arthritis.

7. The method according to claim 6, wherein the patient has plaque psoriasis or moderate to severe plaque psoriasis.

8. The method according to claim 7, wherein the patient has or has not previously been treated with a systemic therapeutic agent for psoriasis prior to treatment with the IL-17A binding agent.

9. The method according to claim 8, wherein the systemic therapeutic agent is selected from methotrexate, cyclosporine, fumarate, acitretin, alefacept, adalimumab, efalizumab, etanercept, infliximab, golimumab and ustekinumab.

10. The method according to claim 6, wherein the patient has active psoriatic arthritis or the patient has co-existing psoriasis.

11. The method according to claim 10, wherein the patient is a TNFi failure or methotrexate failure and/or the patient further receives methotrexate.

12. The method according to claim 6, wherein the patient has moderate to severe active ankylosing spondylitis.

13. The method according to claim 12, wherein the patient is one who has previously been inadequately responsive to treatment with at least one NSAID and/or the patient further receives an NSAID, methotrexate, sulfasalazine, or prednisolone.

14. The method according to claim 1, wherein the IL-17A binding agent comprises a heavy chain framework region (FR) derived from a human germline heavy chain or a mutant sequence thereof, and a light chain framework region (FR) derived from a human germline light chain or a mutant sequence thereof.

15. The method according to claim 1, wherein the IL-17A binding agent is a humanized antibody comprising a heavy chain variable region set forth in SEQ ID NO: 3 or a variant thereof having 1-10 amino acid variations in the FR of the heavy chain variable region, and a light chain variable region set forth in SEQ ID NO: 4 or a variant thereof having 1-10 amino acid variations in the FR of the light chain variable region.

16. The method according to claim 8, wherein the amino acid variations in the heavy chain variable region are A93T and T71A; and/or the amino acid variations in the light chain variable region are F71Y, K49Y, Y36F and L47W.

17. The method according to claim 1, wherein the IL-17A binding agent comprises a light chain set forth in SEQ ID NO: 13 or a variant thereof, and a heavy chain set forth in SEQ ID NO: 14 or a variant thereof.

18. The method according to claim 1, wherein the IL-17A binding agent comprises a heavy chain constant region of human IgG1, IgG2, IgG3, or IgG4 isotype.

\* \* \* \* \*